United States Patent
Slany et al.

(10) Patent No.: US 6,320,055 B1
(45) Date of Patent: Nov. 20, 2001

(54) PROCESS FOR PREPARING HYDANTOINS OR CYCLIC ANHYDRIDES OF AN AMINO ACID

(75) Inventors: Michael Slany, Kirchheim; Michael Schulz; Martin Schäfer, both of Ludwigshafen; Edgar Zeller, Mannheim; Klaus Ebel, Lampertheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/559,046

(22) Filed: Apr. 27, 2000

(30) Foreign Application Priority Data

Apr. 28, 1999 (DE) .............................. 199 19 174

(51) Int. Cl.$^7$ ...................... C07D 263/44; C07D 233/76
(52) U.S. Cl. .................... 548/227; 548/317.1; 548/321.1
(58) Field of Search ................. 548/226, 321.1, 548/317.1, 227

(56) References Cited

U.S. PATENT DOCUMENTS 3,766,266    10/1973    Wakamatsu et al. ................ 562/518

FOREIGN PATENT DOCUMENTS

| 2261853 | 2/1998 | (CA) . |
| 2 115 985 | 10/1971 | (DE) . |
| 196 29 717 | 2/1998 | (DE) . |
| 338 330 | 6/1992 | (EP) . |
| 989122 * | 3/2000 | (EP) . |

OTHER PUBLICATIONS

Arpe, "Industrielle Organische Chemie", 4. Anflage (1994), pp. 312–313.
Beller et al., Chemical Abstracts, 131:102515, 1999.*
Beller et al., J. Org. Chem., 1998, 63, 5658–5661.*

* cited by examiner

Primary Examiner—Fiona T. Powers
(74) Attorney, Agent, or Firm—Keil & Weinkauf

(57) ABSTRACT

Process for preparing compounds of the formula I

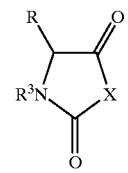

in which R is alkyl or aryl, in each case unsubstituted or substituted, $R^3$ is hydrogen, alkyl or aryl, in each case unsubstituted or substituted, and X=O or NH,
which comprises reacting an aldehyde R—CHO with CO and a compound of the formula II

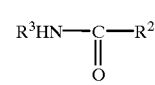

in which $R^2$ is a group which reacts with a —$CO_2H$ group, which is formed during the reaction, with ring-closure to give compounds of the formula I,
in the presence of a transition metal catalyst described.

2 Claims, No Drawings

PROCESS FOR PREPARING HYDANTOINS OR CYCLIC ANHYDRIDES OF AN AMINO ACID

The invention relates to a process for preparing hydantoins or cyclic anhydrides of an amino acid. These compounds are of importance as intermediates for preparing essential amino acids, for example methionine.

The catalytic preparation of N-acylglycine derivatives by reaction of an aldehyde with a carboxamide and carbon monoxide in the presence of a transition metal compound is known.

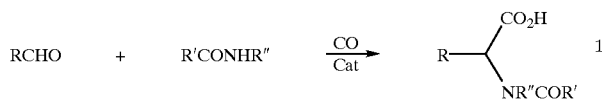

It was initially described by Wakamatsu et al. (DE-A-2115985). The reaction was carried out in the presence of hydrogen/CO gas, at a molar ratio of $CO/H_2=3:1$. The catalyst used was cobalt octacarbonyl at a concentration of 30 mmol of Co metal per liter of reaction mixture.

EP 0 338 330 describes a process for preparing N-acylglycine derivatives using a mixture of a palladium compound and an ionic halide as catalyst. The reaction is carried out at a pressure of 120 bar and a temperature of 120° C.

DE-19629717 describes a catalyst system of the following composition: $PdBr_2/PPh_3/LiCl/H_2SO_4$ for the amido carbonylation of a carboxamide (acetamide) and an aldehyde. The reaction is carried out at a CO pressure of 60 bar and a temperature of 80° C.

To date, the industrial preparation of DL-methionine is carried out in three steps starting with acrolein to which methylmercaptan is added in a base-catalyzed manner to give methylthiopropionaldehyde (methional) (K. Weissermel, H.-J. Arpe, Industrielle Organische Chemie [Industrial Organic Chemistry], 4th Edition (1994), pages 312–313).

The aldehyde is reacted with NaCN and ammonium bicarbonate in aqueous solution at 90° C. to give a hydantoin. In the last step, this compound is converted into the free DL-methionine using NaOH under pressure at 180° C. and acidification with $H_2SO_4$.

It is an object of the present invention to develop, starting from easily obtainable starting materials, a simple synthesis of hydantoins or derivatives thereof, or cyclic anhydrides of amino acids which are potential precursors of essential amino acids, in particular methionine.

We have found that this object is achieved by a process for preparing compounds of the formula I

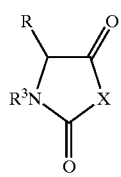

in which R is alkyl or aryl, in each case unsubstituted or substituted, $R^3$ is hydrogen, alkyl or aryl, in each case unsubstituted or substituted, and X=O or NH, which comprises reacting an aldehyde R—CHO with CO and a compound of the formula II

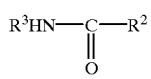

in which $R^2$ is a group which reacts with a —$CO_2H$ group, which is formed during the reaction, with ring-closure to give compounds of the formula I, in the presence of a transition metal catalyst.

$R^2$ is preferably —$NH_2$, —OR' where R' is alkyl or aryl, in particular $C_1$–$C_6$-alkyl or phenyl, or —$O^\ominus NH^\oplus_4$.

R is preferably $C_1$–$C_6$-alkyl where the alkyl radical may carry a functional group, for example —$OCH_3$, —S—$CH_3$, —$NH_2$, in particular —$CH_2Ph$, —$CH_2CH(CH_3)_2$, —$CH(CH_3)$—$CH_2$—$CH_3$, —$CH_2$—$CH_2$—S—$CH_3$, —$(CH_2)_4$—$NH_2$ or phenyl.

The process according to the invention can be outlined as follows:

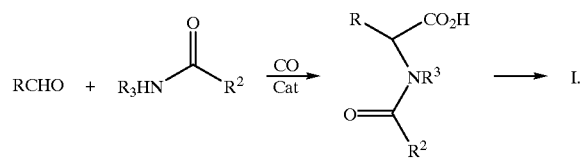

This process has the advantage that starting with an aldehyde and using raw materials which are available industrially on a large scale and are also cheap, for example urea and CO, a hydantoin can be prepared, and furthermore that no salt requiring disposal is produced in the synthesis. The synthesis can be carried out as a one-top process.

One synthesis route can be represented as follows:

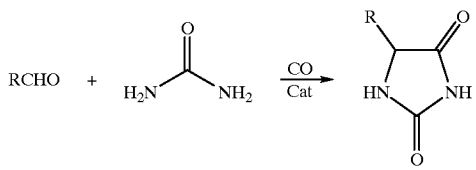

R=alkyl, in particular $CH_2Ph$, $CH_2CH(CH_3)_2$, $CH(CH_3)$ $CH_2CH_3$, $CH(CH_3)_2$, functionalized alkyl radicals, in particular $CH_2$—$CH_2$—SMe, $(CH_2)_4NH_2$, aryl.

Surprisingly, it has been found that in the reaction of urea with aldehydes in the presence of transition metal catalysts, the amido carbonylation to give hydantoins succeeds.

Suitable catalysts are transition metal catalysts which are known per se of the metals Fe, Co, Ni, Ru, Rh, Pd, Os, Ir or Pt.

The catalyst used is preferably a mixture of a palladium compound, an ionic halide and an acid, so that in the overall process, conversions of 100% of the amide at selectivities of upto 98% for the hydantoin are achieved.

Suitable for use as palladium compounds are palladium (II) compounds, Pd(0) compounds or palladium phosphane complexes. Examples of PD(II) compounds are palladium acetates, halides, nitrites, carbonates, ketonates, acetylacetonates and allylpalladium compounds. Particularly preferred representatives are $PdBr_2$, $PdCl_2$, $Li_2PdBr_4$, $Li_2PdCl_4$ and $Pd(OAc)_2$.

Examples of Pd(0) compounds are palladium phosphine and palladium olefin complexes. Particularly preferred representatives are palladium benzylidene complexes and $Pd(PPh_3)_4$.

Bisphosphinepalladium(II) complexes have been found to be particularly useful palladium phosphine complexes. The complexes can be employed as such or be formed in the reaction mixture from a palladium(II) compound, for example PdBr$_2$, PdCl$_2$ or Pd(OAc)$_2$, by addition of phosphanes, for example triphenylphosphane, tritolylphosphane, bis(diphenylphosphino)ethane, 1,3-bis(diphenylphosphino)propane, 1,4-bis(diphenylphosphino)butane.

Particular preference is given to bistriphenylphosphinopalladium(II) bromide or chloride.

Using olefins having one or more chiral centers, it is possible for the reaction to yield isomerically pure or enantiomerically enriched products.

The amount of palladium compound employed is not particularly critical. For the process according to the invention, it has been found that an amount from 0.0001 to 5 mol % of palladium compound (calculated for palladium metal), in particular of from 0.05 to 2 mol %, based on the amide, is sufficient.

The ionic halide used can be, for example, phosphonium bromides or phosphonium iodides, for example tetrabutylphosphonium bromide or tetrabutylphosphonium iodide, and also chlorides, bromides and iodides of ammonium, lithium, sodium and potassium. Preferred halides are bromides and chlorides. The ionic halide is preferably employed in an amount of from 1 to 50 mol %, in particular from 20 to 40 mol %, based on the amide.

The acids used can be organic and inorganic compounds having a pKa<5 (relative to water). Thus, in addition to organic acids, such as p-toluenesulfonic acid, hexafluoropropanoic acid or trifluoroacetic acid, and inorganic acids, such as sulfuric acid or phosphoric acid, it is also possible to use ion-exchange resins, such as Amberlyst or Nafion. Particular preference is given to sulfuric acid. The acid is advantageously employed in an amount of from 0.1 to 20 mol %, in particular from 0.5 to 5 mol %, based on the amide.

Preferred solvents are dipolar aprotic solvents. Examples of these are: sulfoxides and sulfones, for example dimethyl sulfoxide, diisopropyl sulfone or tetrahydrothiophene 2,2-dioxide, 2-methylsulfolane, 3-methylsulfolane, 2-methyl-4-butylsulfolane; esters, such as methyl acetate and butyrolactone; ketones, such as acetone or methyl isobutyl ketone; ethers, such as tetrahydrofuran, anisole, 2,5,8-trioxanonane, dioxane, diphenyl ether and diisopropyl ether, ethylene glycol dimethyl ether; amides, such as dimethylacetamide, DMF and N-methylpyrrolidone; nitriles, such as acetonitrile, and carboxylic acids.

The reaction is generally carried out at pressures of from 0.1 to 200 bar, preferably from 2 to 100 bar, and at temperatures of from 20 to 200° C., preferably at from 50 to 150° C.

A further synthesis route for preparing amino acids or a cyclic anhydride of an amino acid by amidocarbonylation consists in the reaction of urethane with aldehydes in the presence of CO and a transition metal catalyst.

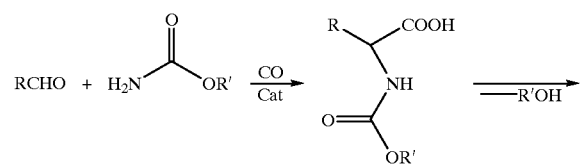

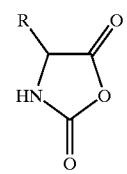

R=alkyl, in particular CH$_2$Ph, CH$_2$CH(CH$_3$)$_2$, CH(CH$_3$)CH$_2$CH$_3$, CH(CH$_3$)$_2$, functionalized alkyl radicals, in particular CH$_2$—CH$_2$—SMe, (CH$_2$)$_4$NH$_2$, aryl R'=alkyl, aryl.

The process has the advantage that, starting with an aldehyde and using the raw materials urethane and CO, which are available industrially on a large scale and are also cheap, an amino acid or a cyclic anhydride of an amino acid can be prepared, and furthermore that no salt requiring disposal is produced in the synthesis.

Surprisingly, it has been found that in the reaction of urethane with aldehydes in the presence of transition metal catalysts, the amidocarbonylation to amino acids or cyclic anhydrides of an amino acid succeeds.

A third synthesis route for preparing hydantoins by amidocarbonylation consists in the reaction of ammonium carbamate (precursor or urea) with aldehydes in the presence of CO and a transition metal catalyst.

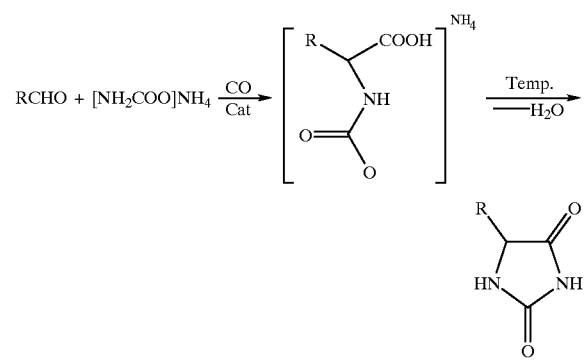

R=alkyl, in particular CH$_2$Ph, CH$_2$CH(CH$_3$)$_2$, CH(CH$_3$)CH$_2$CH$_3$, CH(CH$_3$)$_2$, functionalized alkyl radicals, in particular CH$_2$—CH$_2$—SMe, (CH$_2$)$_4$NH$_2$, aryl.

The process has the advantage that, starting with an aldehyde and using the raw materials ammonium carbamate (urea precursor) and CO, which are available industrially on a large scale and are also cheap, a hydantoin can be prepared with elimination of water, and furthermore that no salt requiring disposal is produced in the synthesis.

Surprisingly, it has been found that in the reaction of ammonium carbamate (urea precursor) with aldehydes in the presence of transition metal catalysts, the amidocarbonylation to hydantoins succeeds with elimination of water.

EXAMPLE

Synthesis of Methionine Via Amidocarbonylation of Urea

1) Amidocarbonylation of methional using urea

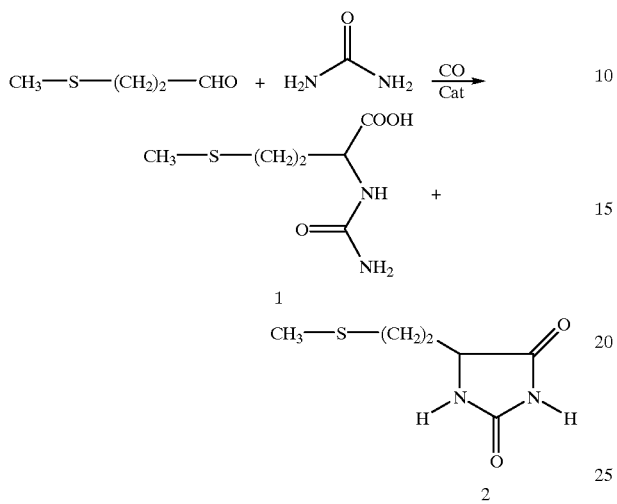

Example for the amidocarbonylation:

67 mg of $PdBr_2$ and 132 mg of $PPh_3$ were dissolved in 75 ml of NMP, and the mixture was stirred for 1 hour. 2.6 g of LiBr, 100 mg of $H_2SO_4$ (conc.), 15 g of triethyl orthoformate, 6.1 g of urea and 10.4 g of methional were then added to the solution, and the mixture was transferred into a 270 ml autoclave. At a CO pressure of 60 bar, the autoclave was heated to 100° C. and operated for 10 hours. After cooling and venting of the autoclave, the liquid discharge was examined by GC analysis.

Methional conversion: 95%
Selectivity hydantoin 2: 86%
Selectivity N-carbamoyl acid 1: 12%

2) Conversion of the hydantoin into D,L-methionine $$\underset{\substack{H\\ \\ O}}{\overset{CH_3-S-(CH_2)_2}{\bigg\langle\!\!\!\bigg\rangle}}\quad\xrightarrow[\substack{2)\ H_2SO_4\\ -CO_2,\ -NH_3}]{1)\ NaOH}\quad \underset{NH_2}{\overset{COOH}{CH_3-S-(CH_2)_2-}}$$

Industrial process (K. Weissermel, H.-J. Arpe, "Industrielle Organische Chemie" [Industrial organic chemistry], 4th edition)

We claim:

1. A process for preparing compounds of the formula I $$\text{I}$$

in which R is alkyl or aryl, in each case unsubstituted or substituted, $R^3$ is hydrogen, alkyl or aryl, in each case unsubstituted or substituted, and X=O, which comprises reacting an aldehyde R—CHO with CO and a compound of the formula II $$R^3HN-\underset{\underset{O}{\|}}{C}-R^2 \qquad \text{II}$$

in which $R^2$ is —OR' where R' is alkyl or aryl, or is a $-O^{\ominus}NH^{\oplus}_4$, in the presence of a transition metal catalyst.

2. A process as claimed in claim 1, wherein R is —$CH_2Ph$, —$CH_2CH(CH_3)_2$, —$CH(CH_3)$—$CH_2$—$CH_3$, —$CH_2$—$CH_2$—$S$—$CH_3$, —$(CH_2)_4$—$NH_2$ or phenyl.

* * * * *